United States Patent [19]

Noack et al.

[11] Patent Number: 5,973,011

[45] Date of Patent: *Oct. 26, 1999

[54] PHARMACEUTICAL PREPARATIONS AND MEDICAMENTS FOR THE PREVENTION AND TREATMENT OF ENDOTHELIAL DYSFUNCTION

[75] Inventors: Eike Albrecht Noack, Neuss; Georg Kojda, Köln, both of Germany

[73] Assignee: ISIS PHARMA GmbH, Zwickau, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/721,465

[22] Filed: Sep. 27, 1996

[30] Foreign Application Priority Data

Mar. 30, 1994 [DE] Germany .............................. 44 10 997
Mar. 28, 1995 [DE] Germany ................ PCT/DE 95/00421

[51] Int. Cl.⁶ .......................... A61K 31/04; A61K 31/44; A61K 31/10; A61K 31/13
[52] U.S. Cl. .......................... 514/742; 514/350; 514/711; 514/740; 514/645; 514/464; 514/642
[58] Field of Search .................... 514/642, 742, 514/645, 350, 711, 740, 464

[56] References Cited

U.S. PATENT DOCUMENTS

5,278,192  1/1994  Fung et al. ............................... 514/645

FOREIGN PATENT DOCUMENTS

92/18002  10/1992  WIPO .............................. A01N 37/12
95/07691  3/1995  WIPO ............................ A61K 31/095

OTHER PUBLICATIONS

M.M. Yaghi et al., *Cardiovasc. Res.*, Jun. 1993, vol. 27, pp. 990–996.

C.G. Sobey et al., *Br. J. Pharmacol.*, Mar. 1992, vol. 105, No. 3, pp. 557–562.

M. Clozel, *Hypertension*, Oct. 1991, vol. 18, No. 4, Suppl., pp. 1137–1142.

G. Kojda et al., *J. Cardiovasc. Pharmacol.*, Jul. 1993, vol. 22, No. 1, pp. 103–111.

K. Schror, *Z. Kardiol.*, 1991, vol. 80, Suppl. 5, pp. 3–6.

K. Higo et al., *J. Pharmacobiodyn.*, Mar. 1992, vol. 15, No. 3, pp. 113–120.

A. Wallace, *J. Card. Surg.*, Mar. 1993, vol. 8, No. 2 Suppl., pp. 325–328 (Abstract).

J. Riezebos et al., *J. Cardiovasc. Pharmacol.*, Mar. 1994, vol. 23, No. 3, pp. 415–423.

A. Wennmalm, *J. Intern Med.*, Apr. 1994, vol. 235, No. 4, pp. 317–327.

P. Jaillon, *La Presse Med.*, Oct. 16, 1986, vol. 15, No. 35, pp. 1747–1753.

J. Abrams, *Am. J. Cardiol.*, Sep. 24, 1992, vol. 70, No. 8, pp. 30B–42B.

R.H. Becker et al., *J. Cardiovaasc. Pharmacol.*, 1991, vol. 18, Suppl. 10, pp. 36–41.

M. Feelisch et al., *Eur. J. Pharmacol.*, Jul. 2, 1987, vol. 139, No. 1, pp. 19–30.

P.J. Henry et al., *Br. J. Pharmacol.*, 1989, vol. 98, pp. 757–766.

G.M. Buga et al., *European Journal of Pharmacology*, 1989, vol. 161, pp. 61–72.

T. Yamakado et al., *Thrombosis Research*, 1982, vol. 26, pp. 135–140.

*Primary Examiner*—Theodore J. Criares
*Attorney, Agent, or Firm*—Marshall, O'Toole, Gerstein, Murray & Borun

[57] ABSTRACT

The present invention describes the use of nitric-oxide-liberating or transferring compounds, stimulators of endogenous NO formation, as well as stimulators of guanylate cyclase, for prevention, treatment and elimination of endothelial dysfunctions and the diseases accompanying these dysfunctions or caused by them, as well as the use of said compounds to produce pharmaceutical products for the cited areas of application.

7 Claims, No Drawings

PHARMACEUTICAL PREPARATIONS AND MEDICAMENTS FOR THE PREVENTION AND TREATMENT OF ENDOTHELIAL DYSFUNCTION

This application claims priority of PCT/DE 95/00421 filed Mar. 28, 1995 and German application P 44 10 99710 filed Mar. 20, 1994.

AREA OF APPLICATION OF THE INVENTION

The invention presented here concerns the use of NO-liberating and/or transferring compounds, stimulator of endogenous NO formation, as well as stimulator of guanylate cyclase for prevention, treatment and elimination of endothelial dysfunctions, as well as diseases that are caused by endothelial dysfunctions or accompany them. Production of pharmaceutical preparations for the cited indications is simultaneously made possible according to the invention.

KNOWN TECHNICAL BACKGROUND

Organic nitrates, like glycerol trinitrate (GTN) (Murrel, Lancet: 80, 113, 151 (1879)), pentaerythrityl tetranitrate (PETN) (Risemann et al., Circulation, Vol. XVII, 22 (1958), U.S. Pat. No. 2,370,437), isosorbide-5-mononitrate (ISMN) (DE-OS 22 21 080, DE-OS 27 51 934, DE-OS 30 28 873, DE-PS 29 03 927, DE-OS 31 02 947, DE-OS 31 24 410, EP-PS 45 076, EP-PS 57 847, EP-PS 59 664, EP-PS 64 194, EP-PS 67 964, EP-PS 143 507, U.S. Pat. No. 3,886,186, U.S. Pat. No. 4,065,488, U.S. Pat. No. 4,417,065, U.S. Pat. No. 4,431,829), isosorbide dinitrate (ISDN) (L. Goldberg, Acta Physiology. Scand, 15, 173 (1948)), propatyl nitrate (Médard, Mem. Poudres 35: 113 (1953)), trolnitrate (FR-PS 984 523) or nicorandil (U.S. Pat. No. 4,200,640) and similar compounds are vasodilators, which have found extensive therapeutic use for decades chiefly in the indication angina pectoris and ischemic heart disease (IHD) (Nitrangin®, Pentalong®, Monolong®, Isoket®, Elantan® and others). Organic nitrates of new types, for example, SPM 3672 (N-[3-nitratopivaloyl]-L-cysteine ethyl ester) (U.S. Pat. No. 5,284,872), as well as its derivatives exhibit, comparable and improved pharmacological efficacy when used in the aforementioned indications. The use of organic nitrites, like isoamyl nitrite, as coronary dilator has also long been known (Brunton, Lancet, 97 (1867)). Other NO-liberating or transferring compounds, like thionitrites, thionitrates, S-nitrosothiols or nitrosoproteins (Harrison et al., Circulation, 87:1461–1467 (1993), as well as substituted furoxanes (1,2,5-oxadiazole-2-oxide, furazan-N-oxide) (Feelisch al., Biochem. Pharmacol. 44:1149–1157 (1992) or substituted sydnonimines, especially molsidomine (DE-AS 16 95 897, DE-AS 25 32 124, DD-PS 244 980), are also described as potent coronary dilators. All these substances themselves or in the form of pharmacologically active metabolites, for example, the molsidomine metabolites SIN 1 and SIN 1A (Noack Nitroglycerin VII, Walter de Gruyter & Co., Berlin, 1991, 23–28), as well as their derivatives and structural analogs (Noack and Feelisch, Molecular mechanism of nitrovascular bioactivation, in "Endothelial Mechanisms of Vasomotor Control" (editors Drexler et al.), pp. 37–50, Steinkopff Verlag, Darmstadt, FRG (1991)), are capable of in vivo liberation or transfer of nitric oxide.

The galenic processing of organic nitrates and nitrites, as well as other NO-liberating or transferring compounds to pharmaceutical preparation for treatment of angina pectoris and ischemic heart disease is generally known. It occurs according to procedures and rules generally familiar to pharmaceutical experts, in which selection of the technologies to be applied and the galenic auxiliaries to be employed is primarily guided according to the active principle being processed. Questions of chemical-physical properties, the chosen form of administration, the desired effect time, as well as avoidance of drug auxiliary incompatibilities are of special significance here. Peroral, parenteral, sublingual or transdermal administration in the form of tablets, coated tablets, capsules, solutions, sprays or plasters is primarily described for drugs with the indication angina pectoris and ischemic heart disease (DD-PS 293 492, DE-AS 26 23 800, DE-OS 33 25 652, DE-OS 33 28 094, DE-PS 40 07 705, DE-OS 40 38 203, JP Application 59/10513 (1982)).

In addition to the applications of nitrosylating substances that have been known for years, their use to treat and prevent diseases caused by pathologically increased concentrations of sulfur-containing amino acids in body fluids is also described. These disease entities, caused by congenital or acquired defects in metabolism of these amino acids and characterized by increased blood and urine concentrations of said amino acids (homocystinuria), are combined under the term homocysteinemia [sic] * (WO 92/18002).

The antiischemic effectiveness of organic nitrates and the other aforementioned substance classes is explained by hemodynamic effects, especially a heart-unloading effect that leads to economy of oxygen consumption of the heart or corrects the imbalance between $O_2$ supply and demand present in IHD. The cause is preferred expansion of venous pooling and a reduction in preload with a direct coronary dilatation effect, especially in the area of coronary stenosis. The post-stenotic reduced perfusion could be favorably influenced precisely by this (positive steal effect) since the organic nitrates obviously have a more potent effect in atherosclerotic vessels than in healthy vessels (Koida et al., Endothelium 1 (supplement): Abstract 299, p. s76 (1993)), especially in the area of coronary stenoses. This purely hemodynamic effect is mediated by radical nitric oxide (NO·), which is uniformly liberated from all nitrovasodilators despite the very different chemical structure of the compounds. The bioactivation pathways that ultimately lead to production of NO· in situ, i.e., in the endothelial cells and smooth muscle cells of the vessel, are very different, however (Noack and Feelisch, Molecular mechanism of nitrovascular bioactivation, in: "Endothelial Mechanisms of Vasomotor Control" (editors Drexler et al.), pp. 37–50, Steinkopff Verlag, Darmstadt, FRG (1991)). This was clarified beyond question in recent years by direct NO measurement by different techniques (method of Noack et al., Neuroprotocols, 1:133–139 (1992)). NO has a vasodilatory effect by activating soluble guanylate cyclase. Formation of cGMP from GTP is stimulated by this. cGMP in turn leads to various phosphorylation reactions (e.g., on protein kinases) that promote intracellular Ca storage (Karczewski et al., Z. Kardiol. 79 (supplement 1):212 (1990)). Relaxation then occurs from the reduction in intracellular free $Ca^{2+}$ level. It has been known since 1987 that the endothelium derived relaxing factor (EDRF) is identical to NO or an NO-containing substance (Palmer et al., Nature, 327:524–526 (1987); Ignarro et al., Proc. Natl. Acad. Sci. 84, 9265–9269 (1987)) and has important significance for local blood supply.

*[Translator's note: homocystinemia?]

The endothelial cells form a continuous monolayer in the region of the internal wall of a blood vessel. This results in a total surface of about 800 $m^2$ for an adult person with an intrinsic weight (1.5 to 2 kg) corresponding to that of the human liver. According to the present view, the functions exerted by the endothelial cells are of two kinds: mechanical and functional. On the one hand, they exert a sort of barrier function with which penetration of blood components, like low-density lipoproteins (LDL), into the vessel wall near the lumen (intima) is supposed to be prevented. On the other hand, they possess an endocrine function. Increased synthesis of bioactive substances occurs from different stimuli, like EDRF/NO and prostaglandin-$I_2$ ($PGI_2$) with which the function of the flowing cells (Pohl and Busse, Eur. Heart J., 11 (supplement B), 35–42 (1990)) regional hemodynamics (Furchgott, Circ. Res. 53:557–573 (1983)) and the structure of the vessel wall (Di Corleto, Exp. Cell Res. 153:167–172 (1984)) are fundamentally influenced. The fact that a pathological effect on endothelial function that can have different consequences invariably occurs during damage to the endothelium for any reason (endothelial damage from hypercholesterolemia (T. J. Verbeuren et al., Circ. Res. 58:552–564 (1986)), endothelial damage in the postinfarction phase (M. R. Sigreid et al., Circ. 86 (supplement 1) :21 (1992)) is thus explained informally at the same time. Regional vasoconstriction and vasospasm and reconstruction or growth processes in the vessel wall that are viewed as initial processes of atherogenesis are included here.

Endothelial dysfunction is generally characterized by a limitation or loss of physiological vasodilation mediated by the endothelium. A reduction or increase in NO-mediated vessel relaxation, vascular protection mediated by NO and growth processes suppressed by NO in the intima and media is observed simultaneously. Endothelial dysfunction is also characterized by proliferative processes in the vessel wall as a result of increased mitogenesis, increased endothelial adhesion and migration of leukocytes and macrophages, as well as increased oxidation of low density lipoproteins (LDL), which damage the endothelium. It is regularly observed in pathophysiological states within the scope of atherosclerosis, hypertension, hypercholesterolemia, diabetes mellitus and cardiac insufficiency (Creager et al., J. Clin. Invest. 86, 228–234 (1990); Linder et al., Circulation 81:1762–1769 (1990); Zeiher et al., Circulation 83:391–401 (1991)). Hypoxia and limited shear forces are also triggering events for an endothelial dysfunction. Among other things, it leads to a situation in which vasoactive substances, like acetylcholine or serotonin, which normally produce vasorelaxation, cause vasoconstriction because of their direct vasoconstrictive effects on smooth vascular musculature, which adversely affects the disease picture (Golino et al., N. Engl. J. Med. 324:641–648 (1991)). Physiological vasomotor regulation is therefore not just disturbed during endothelial dysfunction, but in fact reversed. These changes are even more pronounced during atherosclerotic reconstruction of the internal wall of the vessel (Ludmer et al., N. Engl. J. Med. 315:1046–1051 (1986)).

With its autocrine and paracrine activity, the endothelium contributes not only to maintaining health of the wall of the blood vessel, but also influences the effect of exogenous NO liberators, like PETN or GTN, by forming EDRF/NO itself. If the endothelium is removed, for example, mechanically, from the wall of the artery (during invasive catheter diagnosis or extracorporeally on isolated vessel segments), or if endothelial NO formation is suppressed by specific inhibitors, the vasodilative effect of nitrovasodilators like GTN or PETN is intensified (Busse et al., Cardiovasc. Pharmacol. 14 (supplement 11) :S81–S85 (1989); Kojda et al., J. Vasc. Res. 29:151 (1992A)). Pharmacological inhibition of endothelial NO synthesis leads to the same effect on coronary veins (Kojda et al., Naunyn-Schmiedeberg Arch. Pharmacol. 346:R35 (1992B)). It is known that the effect of calcium antagonists, especially those of the 1,4-dihydropyridine type (DHPs), is weakened after removal of the endothelium (Kojda et al., Bas. Res. Cardiol. 86:254–256 (1991)). Further studies have shown that these substances are probably stimulators of endothelial NO formation and liberation (Günther et al., Basic Res. Cardiol. 87:452–460 (1992)). Kinins, like bradykinins, also exert their biological activity via increased endothelial formation and liberation of EDRF/NO (V. A. Briner et al., Am. J. Physiol. 264:F322–F327 (1993); Kelm et al., Biochem. Biophys. Res. Commun. 154:236–244 (1988)).

PRESENTATION OF THE INVENTION

Endothelial dysfunctions are today viewed as the triggering mechanisms of common and pathophysiologically significant cardiovascular diseases, like atherosclerosis. Prevention, treatment and elimination of these dysfunctions and the diseases accompanying them or caused by them therefore represent important therapeutic necessities.

It has now been found that the use of NO-liberating and/or transferring compounds, stimulator of endogenous NO formation, as well as stimulator of guanylate cyclase, especially stimulator of soluble guanylate cyclase is suitable for prevention, treatment and elimination of endothelial dysfunctions, as well as diseases accompanying these dysfunctions and/or caused by them. These endothelial dysfunctions and diseases are primarily endothelial damage from hypercholesterolemia, endothelial damage from hypoxia, endothelial damage from mechanical and chemical noxae, especially during and after drug and mechanical reopening of stenosed vessels, for example, following percutaneous transluminal angiography (PTA) and percutaneous transluminal coronary angiography (PTCA), endothelial damage in the postinfarction phase (endothelial dysfunction during reperfusion), endothelium-mediated reocclusion following bypass operation, blood supply disturbances in peripheral arteries, as well as cardiovascular diseases, like atherosclerosis, hypertension, including pulmonary and portal hypertension, hypertensive heart disease, diabetic micro- and macroangiopathy, coronary heart disease, cardiac insufficiency or other diseases that are causally due to endothelial dysfunctions.

NO-liberating and/or transferring compounds, stimulators of endogenous NO formation, as well as stimulators of guanylate cyclase according to this invention are, among other things, compounds that act directly or indirectly on guanylate cyclase, in which compounds that can liberate a stimulator of guanylate cyclase or increase its enzyme-effective concentration in some other way and/or act antagonistically relative to inhibitors of guanylate cyclase or reduce its enzyme-effective concentration in some other way are interpreted as indirect stimulators of guanylate cyclase. Compounds that are suitable for increasing endogenous NO formation or liberation, like calcium antagonists, especially those of the 1,4-dihydropyridine type, for example, nefedipine, felodipine, nimodipine, amlodipine and others, are used as indirect stimulators of guanylate cyclase. Use of compounds that can increase endothelial kinin content is also suitable. These are primarily stimulators of kinin receptors, like kinins or substances with similar action, stimulators of endothelial kinin formation, as well as inhibitors of kinin breakdown, especially inhibitors of the angiotensin converting enzyme (ACE inhibitor), like captopril, enalapril, moexipril, ramipril and related active principles. The use of compounds that exhibit their effect generally by liberating and/or transferring endogenous or exogenous nitric oxide is the particularly preferred variant in the present invention. Substance classes and compounds that are considered in particular include organic nitrates, especially glycerol trinitrate, pentaerythrityl tetranitrate, isosorbide-5-mononitrate, isosorbide dinitrate, mannitol hexanitrate, inositol hexanitrate, propatyl nitrate, trolnitrate, nicorandil, newer nitrates, like SPM 3672, as well as their pharmacologically compatible derivatives, organic nitrites, like isoamyl nitrite, thionitrites, thionitrates, S-nitrosothiols, like S-nitroso-N-acetyl-D,L-penicillamine, nitrosoproteins, NO-liberating furoxane derivatives, NO-liberating sydnonimine derivatives, especially molsidomine, mesocarb, as well as their analogs, nitrosyl complex compounds, especially iron-nitrosyl compounds, like nitroprusside sodium, as well as nitric acid itself. Since the nitric oxide liberation and/or transfer often occurs here in vivo via pharmacologically active metabolites, these are also suitable in principle for use according to the present invention. The use of pharmacologically compatible derivatives of all the aforementioned compounds is also possible. Common addition compounds, salts or enzymatically or hydrolytically cleavable compounds, like esters, amides and similar compounds represent possible variations in particular.

Choice of a corresponding active principle is guided according to general pharmacological principles and therapeutic requirements familiar to one skilled in the art. State of health, stage of the disease, physical condition, known effects and side effects, contraindications, treatment frequency and application time, drug interactions, as well as parallel drug use, are to be considered in addition to the desired pharmacological effect.

Dosage occurs in the corresponding therapeutic doses, which are based on those in which the corresponding active principles are already used for known indications. The total daily dose can be as much as 500 mg depending on the active ingredient. Daily doses of up to 350 mg are generally sufficient. The dosage and dosage range are to be chosen so that therapeutic plasma levels, which are as constant as possible are built up. The compounds employed according to the invention can be supplied for use themselves or combined as part of a galenic preparation as individual active ingredients or in combination with each other or with known cardiovascular therapeutics, for example ACE inhibitors, antiatherosclerotics, antihypertensives, beta-blockers, cholesterol reducers, diuretics, calcium antagonists, coronary dilators, lipid reducers, peripheral vasodilators, thrombocyte aggregation inhibitors or other substances also used as cardiovascular therapeutics.

Production of the galenic preparations occurs according to procedures and rules generally familiar to the pharmaceutical expert, in which choice of the technologies to be applied and the galenic auxiliaries to be employed is primarily guided according to the active ingredient being processed. Questions of chemical-physical properties, chosen form of administration, desired effect time, type of effect, as well as avoidance of drug-auxiliary incompatibilities are of special significance here. It therefore falls to the expert to choose in routine fashion the drug form, auxiliary and preparation method with reference to known material and process parameters. The corresponding drug form should be configured so that it contains the corresponding active ingredient in an amount that permits the daily dose to be distributed in controlled-release systems to one to two individual doses and in other drug forms to as much as 10 individual doses in order to achieve a constant therapeutic plasma level. Continuous administration by long-term infusion is also suitable.

The cited compounds according to the invention can be administered primarily orally, intravenously, parenterally, sublingually or transdermally. The corresponding drug preparation is preferably produced in liquid or solid form. Solutions are suitable for this purpose, especially for preparation of drops, injections or aerosol sprays, in addition to suspensions, emulsions, syrups, tablets, film tablets, coated tablets, capsules, pellets, powders, pastilles, implants, suppositories, creams, gels, salves, plasters or other transdermal systems.

The pharmaceutical preparations contain ordinary galenically employable, organic or inorganic carriers and auxiliaries, which themselves are chemically inert relative to the corresponding active ingredients. Water, salt solutions, alcohols, vegetable oils, polyethylene glycols, gelatins, lactose, amylose, magnesium stearate, talc, highly dispersed silicon dioxide, paraffin, fatty acid mono- and diglycerides, cellulose derivatives, polyvinylpyrrolidone and similar compounds are suitable for this purpose without being limited to them. The preparation can be sterilized and, if necessary, mixed with auxiliaries, like fillers, binders, lubricants, mold release agents, mold lubricants, decomposition, moisture-retaining, adsorption or antiexplosion agents, preservatives, stabilizers, emulsifiers, solubilizers, salts to influence osmotic pressure, buffer solutions, dyes, fragrances, flavorings or sweeteners. The pharmaceutical expert will make an appropriate choice to avoid drug-auxiliary incompatibilities with reference to known material parameters.

A new therapeutic possibility to counteract pathological situations that promote endothelial dysfunction, like hypoxia, high serum cholesterol level, increased blood pressure, diabetes, post-stenotic reperfusion, e.g., during myocardial infarction, and mechanical and chemical noxae, or to entirely prevent the development of endothelial dysfunction is offered with the proposed invention. Therapeutic use of appropriate compounds in whatever galenic preparation therefore permits, as discussed, prevention and actual therapy of cardiovascular diseases of this etiology for the first time, like atherosclerosis and the diseases resulting from it. These include coronary heart disease, vascular stenoses and blood supply disorders in peripheral arteries, micro- and macroangiopathies in diabetes mellitus, etc. The aforementioned compounds surprisingly exhibit an endothelium-protecting effect that is independent of the previously known effects, especially the purely hemodynamic and antiischemic properties of, say organic nitrates, or their effectiveness in homocysteinemia. Their use is therefore capable of stopping these pathological processes or even causing them to decline as long as they are still not irreversible. These are therefore unexpected, novel effect components that have not been described thus far and were not to be expected in this form.

The following examples will further explain the invention with respect to its essence and execution without, however, limiting it in its scope.

PRACTICAL EXAMPLES

Example 1

Experiments on a pharmacological in vivo model (New Zealand rabbits).

Cholesterol feeding is suitable in an animal experiment to produce endothelial dysfunction within weeks to months, permitting investigation and quantification of the effects of a drug (Jayakody et al., Can. J. Physiol. Pharmacol. 63:1206–1209 (1985); Verbeuren et al. Circ. Res. 58:552–564 (1986); Freiman et al., Circ. Res. 58:783–789 (1986)).

Groups of nine female New Zealand rabbits were fed a standard diet or a cholesterol-enriched (0.75%) feed (40 g/kg/day) over a period of 15 weeks. Cholesterol feeding led to an increase of plasma level from 69.8±10.4 to 907.1±85.5 mg/dL and produced atherosclerotic lesions in the region of the aorta, which were quantified after staining with Sudan IV by means of computer-assisted laser scanning technique. The aortal changes encompassed a surface of 73.3±1.9% on the arch of the aorta, one of 46.3±2.5% on the thoracic aorta and 49.6±3.5% in the region of the abdominal aorta (FIG. 2, control).

Example 2

The atherosclerotically damaged vessels exhibited unchanged contraction capability to phenylephrine, but endothelial-mediated vasorelaxation after administration of 1 $\mu$m acetylcholine was altered in its function in comparison with the controls (standard diet) in a way that can best be described as endothelial dysfunction. The segments of the thoracic aorta of the cholesterol-fed animals (+) exhibited significantly weaker sensitivity to acetylcholine than the aortal segments of the control animals (FIG. 1). The degree of measured endothelial dysfunction correlated directly with the corresponding severity of the atherosclerotic lesions (r=0.67, p<0.0001) (FIG. 3). These data demonstrate that endothelial dysfunction developed after feeding with cholesterol.

Example 3

Two additional groups of nine female New Zealand rabbits each additionally received pentaerythrityl tetranitrate (PETN) (6 mg/kg/day), in which the drug was incorporated into the pelletized feed. A significant reduction of atherosclerotic lesions occurred in the animals simultaneously treated with PETN. The extent of these lesions was determined according to Example 1. A significantly reduced percentage of atherosclerotic damage was found in all parts of the aorta (aortal arch: 58.6±2.1%, thoracic aorta 34.7±2.0% and abdominal aorta 39.3±3.1%) (FIG. 2).

Example 4

No significant difference in maximum (1 $\mu$M acetylcholine) endothelium-mediated relaxation was observed any longer after PETN feeding in comparison with the animals not fed cholesterol (endothelial dysfunction) so that these results indicate a distinct protective effect of the nitrovasodilator PETN, since this inhibited endothelial dysfunction in the sense of the present invention (FIGS. 3 and 4, Table 1).

Comparison between FIGS. 3 and 4 shows that PETN can reduce the degree of atherosclerotic lesions and improve endothelial function. The poorer correlation coefficient in the PETN group indicates that PETN also leads to a dissociation of the close relation between atherosclerotic lesions and endothelial function.

Table 1 shows the effect of PETN (6 mg/kg/day) on the development of endothelial dysfunction in the thoracic aorta of white New Zealand rabbits, which was induced by feeding of a cholesterol diet (0.75%; 15 weeks). The effect strength of the endothelial-dependent vasodilator acetylcholine is expressed as concentration (in log M; $pD_2$ value) that antagonized half of the effect of the vasoconstrictor phenylephrine during cumulative administration (the higher this value, the stronger the effect of acetylcholine). The maximum dilative effect is expressed as percentage of effect of the vasoconstrictor phenylephrine, which was antagonized at the maximum effective concentration of acetylcholine (1 $\mu$M). The endothelial dysfunction induced by cholesterol feeding alone (control) is recognizable in the significantly reduced effect strength and maximum effect of acetylcholine (*, p<0.05). With simultaneous feeding of PETN the differences can no longer be detected. Moreover, PETN significantly improves (#, p<0.05) the effect strength of acetylcholine and thus endothelial function after cholesterol feeding, whereas a significant deterioration in endothelial function occurs after standard feeding. Overall this demonstrates the protective effect of PETN on endothelial function in experimentally induced atherosclerosis. Resorption and flow of PETN in the plasma can also be demonstrated 24 hours after the last feeding of the animals with reference to the measured concentrations of the metabolite pentaerythrityl mononitrate (PEMN) in the plasma (FIG. 5).

TABLE 1

|  | Control | | PETN | |
|---|---|---|---|---|
|  | Standard | Cholesterol | Standard | Cholesterol |
| Effect strength of acetylcholine ($pD_2$ value) | 6.91 ± 0.02 | 6.12 ± 0.05* | 6.62 ± 0.06# | 6.47 ± 0.13# |
| Maximum dilative effect of acetylcholine (%) | 84.8 ± 1.2 | 60.7 ± 8.5* | 74.7 ± 4.9* | 65.0 ± 4.7 |

Example 5

A typical tablet has the composition:

| Pentaerythrityl tetranitrate | ISIS PHARMA | 20 mg |
| Lactose | DAB** 10 | 137 mg |
| Potato starch | DAB 10 | 80 mg |
| Gelatin | DAB 10 | 3 mg |
| Talc | DAB 10 | 22 mg |
| Magnesium stearate | DAB 10 | 5 mg |
| Silicon dioxide, highly dispersed | DAB 10 | 6 mg |
| | | 273 mg |

**German Pharmacopoeia.

Example 6

A tablet with a content of 20 mg pentaerythrityl trinitrate (PETriN) has the composition:

| PETriN | | 20 mg |
| Lactose | DAB 10 | 137 mg |
| Potato starch | DAB 10 | 80 mg |
| Gelatin | DAB 10 | 3 mg |
| Talc | DAB 10 | 22 mg |
| Magnesium stearate | DAB 10 | 5 mg |
| Silicon dioxide, highly dispersed | DAB 10 | 6 mg |
| | | 273 mg |

Example 7

A tablet with a content of 20 mg pentaerythrityl dinitrate (PEDN) has the composition:

| | | |
|---|---|---|
| PEDN | | 20 mg |
| Lactose | DAB 10 | 137 mg |
| Potato starch | DAB 10 | 80 mg |
| Gelatin | DAB 10 | 3 mg |
| Talc | DAB 10 | 22 mg |
| Magnesium stearate | DAB 10 | 5 mg |
| Silicon dioxide, highly dispersed | DAB 10 | 6 mg |
| | | 273 mg |

Example 8

A tablet with a content of 20 mg erythrityl tetranitrate (ETN) has the composition:

| | | |
|---|---|---|
| ETN | | 20 mg |
| Lactose | DAB 10 | 137 mg |
| Potato starch | DAB 10 | 80 mg |
| Gelatin | DAB 10 | 3 mg |
| Talc | DAB 10 | 22 mg |
| Magnesium stearate | DAB 10 | 5 mg |
| Silicon dioxide, highly dispersed | DAB 10 | 6 mg |
| | | 273 mg |

Example 9

A tablet with a content of 20 mg isosorbide mononitrate (ISMN) has the composition:

| | | |
|---|---|---|
| ISMN | | 20 mg |
| Lactose | DAB 10 | 137 mg |
| Potato starch | DAB 10 | 80 mg |
| Gelatin | DAB 10 | 3 mg |
| Talc | DAB 10 | 22 mg |
| Magnesium stearate | DAB 10 | 5 mg |
| Silicon dioxide, highly dispersed | DAB 10 | 6 mg |
| | | 273 mg |

Example 10

A tablet with a content of 20 mg isosorbide dinitrate (ISDN) has the composition:

| | | |
|---|---|---|
| ISDN | | 20 mg |
| Lactose | DAB 10 | 137 mg |
| Potato starch | DAB 10 | 80 mg |
| Gelatin | DAB 10 | 3 mg |
| Talc | DAB 10 | 22 mg |
| Magnesium stearate | DAB 10 | 5 mg |
| Silicon dioxide, highly dispersed | DAB 10 | 6 mg |
| | | 273 mg |

Example 11

A tablet with a content of 40 mg pentaerythrityl tetranitrate (PETN) and 40 mg propranolol hydrochloride has the composition:

| | |
|---|---|
| PETN | 40 mg |
| Propranolol hydrochloride | 40 mg |
| Lactose | 224 mg |
| Potato starch | 80 mg |
| Gelatin | 3 mg |
| Talc | 22 mg |
| Magnesium stearate | 5 mg |
| Silicon dioxide, highly dispersed | 6 mg |
| | 420 mg |

Cholesterol Feeding
Standard

Acetylcholine (−log M)

FIG. 1. Development of endothelial dysfunction after feeding white New Zealand rabbits with a cholesterol diet (0.75%; 15 weeks). The vasorelaxing effect of the endothelium-dependent vasodilator acetylcholine is shown and thus the functional capability of the endothelium expressed as percentage of precontractions still remaining at each given concentration, which was triggered by the vasoconstrictor phenylephrine.

Atherosclerotic Surface (%)
Control

Aortal Arch Thoracic Aorta Abdominal Aorta

FIG. 2. Degree of atherosclerotic lesions on the luminal surface of different sections of the aorta after feeding of a cholesterol diet (0.75%; 15 weeks) (without control) and simultaneous administration of PETN (6 mg/kg/day). The atherosclerotic lesions were stained with Sudan IV and the percentage of stained surface (refer to the total surface) determined by means of a computer-assisted laser scanning method. PETN causes a significant reduction in formation of atherosclerotic lesions ($p<0.05$).

Relaxation from acetylcholine (1 $\mu$M) (%)
Atherosclerotic Surface (%)

FIG. 3. Relation between degree of atherosclerotic lesions on luminal section of segments of the thoracic aorta after feeding of a cholesterol diet (0,75%; 15 weeks) and the maximum relaxation determined beforehand in the same segment induced by 1 $\mu$M acetylcholine (endothelial function). The greater the surface of the lesions, the worse the relaxation or endothelial function.

Relaxation from acetylcholine (1 $\mu$M) (%)
Atherosclerotic surface (%)

FIG. 4. Same representation as in FIG. 3 after simultaneous feeding of cholesterol and PETN.

FIG. 5. Plasma level of pentaerythrityl mononitrate in plasma of white New Zealand rabbits after 24 hours of feed withdrawal before blood sampling, which preceded the acute experiment. The standard feed contained pentaerythrityl tetranitrate (150 mg/kg) in both cases and additionally 0.75% cholesterol in the cholesterol group. The concentration of pentaerythrityl mononitrate was quantitatively determined by gas chromatography/mass spectroscopy after processing of the plasma samples.

We claim:

1. A method of treating endothelial dysfunctions caused by hypercholesterolemia, said method comprising administration of 6 mg/kg/day of an organic nitrate to an individual to maintain or improve endothelial function.

2. The method of claim 1 wherein the organic nitrate is selected from the group consisting of glycerol trinitrate, pentaerythrityl tetranitrate, isosorbide-5-mononitrate, isosorbide dinitrate; mannitol hexanitrate, inositol hexanitrate, propatyl nitrate, trolnitrate, nicorandil or SPM 3672, and pharmacologically compatible derivatives.

3. The method of claim 1 wherein the organic nitrate is used in pharmaceutical preparations for treating endothelial dysfunctions.

4. The method of claim 3 wherein the organic nitrate is combined with active compounds used to treat cardiovascular diseases.

5. The method of claim 4 wherein the active compound to treat cardiovascular diseases is selected from the group consisting of ACE inhibitors, antiatherosclerotics, antihypertensives, beta-blockers, cholesterol reducers, diuretics, calcium antagonists, coronary dilators, lipid reducers, peripheral vasodilators and thrombocyte aggregation inhibitors.

6. The method of claim 2 wherein the organic nitrate comprises pentaerythrityl tetranitrate (PETN).

7. A method of treating endothelial damage attributed to hypercholesterolemia comprising administration of a 6 mg/kg/day an organic nitrate to an individual to maintain or improve endothelial function.

* * * * *